United States Patent
Capet et al.

(10) Patent No.: US 11,078,183 B2
(45) Date of Patent: *Aug. 3, 2021

(54) TETRAHYDRATE OF H3 LIGAND, ITS PROCESS OF PREPARATION AND PHARMACEUTICAL COMPOSITIONS COMPRISING THE SAME

(71) Applicant: BIOPROJET, Paris (FR)

(72) Inventors: Marc Capet, Melesse (FR); Jeanne-Marie Lecomte, Paris (FR); Jean-Charles Schwartz, Paris (FR)

(73) Assignee: BIOPROJET, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/496,013

(22) PCT Filed: Mar. 20, 2018

(86) PCT No.: PCT/EP2018/056999
§ 371 (c)(1),
(2) Date: Sep. 20, 2019

(87) PCT Pub. No.: WO2018/172344
PCT Pub. Date: Sep. 27, 2018

(65) Prior Publication Data
US 2020/0024256 A1   Jan. 23, 2020

(30) Foreign Application Priority Data
Mar. 21, 2017 (EP) ..................... 17305310

(51) Int. Cl.
*C07D 401/12* (2006.01)
(52) U.S. Cl.
CPC ................. *C07D 401/12* (2013.01)
(58) Field of Classification Search
CPC .................................. C07D 401/12
See application file for complete search history.

(56) References Cited

U.S. PATENT DOCUMENTS

2020/0030310 A1*  1/2020  Ligneau ............... A61P 25/26
2020/0093738 A1*  3/2020  Lecomte ............. A61K 9/0053

FOREIGN PATENT DOCUMENTS

WO     2006/117609 A2    11/2006

OTHER PUBLICATIONS

Khankari; Thermochimica Acta 1995, 248, 61-79. DOI: 10.1016/0040-6031(94)01952-D (Year: 1995).*
International Search Report issued in corresponding International Patent Application No. PCT/EP2018/056999 dated May 2, 2018.
European Search Report issued in corresponding European Patent Application No. EP 17 30 5310 dated Jun. 20, 2017.
Byrn S., et al., "Pharmaceutical Solids: A Strategic Approach to Regulatory Considerations" Pharmaceutical Research, 12(7):Jul. 1995, pp. 945-954, XP000996386 (cited in EPSR and ISR).
Hilfiker R., et al., "Polymorphism in the Pharmaceutical Industry" Jan. 2006, pp. 1-19, XP002528052 (cited in EPSR and ISR).
Caira, M. R., "Crystalline Polymorphism of Organic Compounds" Topics in Current Chemistry, 198:Jan. 1998, pp. 163-208, XP001156954 (cited in EPSR and ISR).
Hilfiker, R., et al. "Relevance of Solid-state Properties for Pharmaceutical Products" Polymorphism: in the Pharmaceutical Industry, pp. 1-19 (2006) XP-002528052.
Morissette. S. L., et al. "Elucidation of crystal form diversity of the HIV protease inhibitor ritonavir by high-throughput crystallization" PNAS, 100(5):2180-2184 (Mar. 4, 2003).

* cited by examiner

*Primary Examiner* — Daniel R Carcanague
(74) *Attorney, Agent, or Firm* — Troutman Pepper Hamilton Sanders LLP

(57) ABSTRACT

The present invention concerns the tetrahydrate form of the compound: (3S)-4-{4-[3-(3-methylpiperidin-1-yl)propoxy]phenyl}pyridine 1-oxide, dihydrochloride, its process of preparation and therapeutical uses thereof.

11 Claims, 2 Drawing Sheets

TETRAHYDRATE OF H3 LIGAND, ITS PROCESS OF PREPARATION AND PHARMACEUTICAL COMPOSITIONS COMPRISING THE SAME

CROSS REFERENCE TO RELATED APPLICATIONS

This is a U.S. National Phase Application under 35 U.S.C. § 371 of International Patent Application No. PCT/EP2018/056999, filed Mar. 20, 2018, which claims priority of European Patent Application No. 17305310.9, filed Mar. 21, 2017. The entire contents of which are hereby incorporated by reference.

FIELD OF THE INVENTION

The present invention concerns the tetrahydrate form of H3 ligand of formula (A):

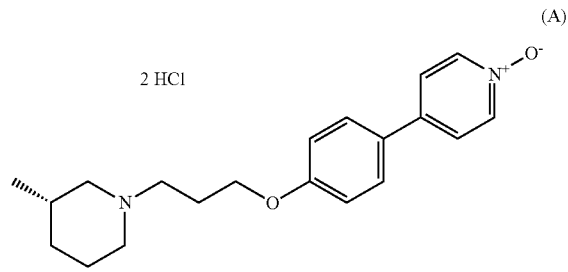 [SMILES: C[C@H]1CCCN(CCCOc2ccc(-c3cc[n+]([O-])cc3)cc2)C1]

(A)

The invention also concerns the process of preparation of said tetrahydrate of compound (A), the pharmaceutical compositions containing the same, and their therapeutical uses.

Compound of formula (A) is (3S)-4-{4-[3-(3-methylpiperidin-1-yl)propoxy]phenyl}pyridine 1-oxide, dihydrochloride.

BACKGROUND

It is disclosed along with its free base form, its oxalate and hydrochloride in WO 2006/117609, where many other non-imidazole histamine H3 ligands and their therapeutical uses are disclosed.

Among the disclosed H3 ligands, (3S)-4-{4-[3-(3-methylpiperidin-1-yl)propoxy]phenyl}pyridine 1-oxide has been found to be very potent. However, it is liquid and not favored for pharmaceutical uses.

The oxalate salt thereof is not suitable either as a drug candidate as oxalate salts may lead to deposits of calcium oxalate.

The monohydrochloride salt thereof melts at 74° C. and likely to melt during compression when preparing pills. It is therefore expected to be unsuitable either for further development.

The dihydrochloride salt was found to be too hygroscopic to meet the stability requirements for pharmaceuticals.

Therefore, none of the forms of compound (A) is suitable for pharmaceutic uses.

SUMMARY

Unexpectedly, it was found that the tetrahydrate of compound (A) was highly stable, and crystalline, with a high melting point, thus meeting the necessary requirements for a drug candidate.

According to a first object, the present invention thus concerns the tetrahydrate form of compound of formula (A).

The expression "tetrahydrate of compound (A)" refers to the chemical entity comprising one molecule of compound (A) and four molecules of water.

The "base of compound (A)" refers to the following compound:

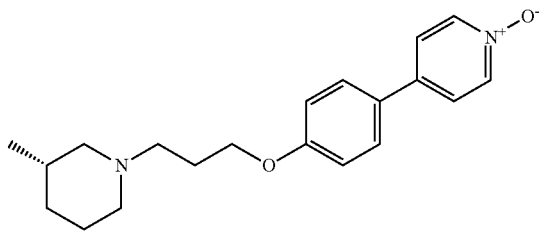 [SMILES: C[C@H]1CCCN(CCCOc2ccc(-c3cc[n+]([O-])cc3)cc2)C1]

The tetrahydrate form of compound (A) may exist in a crystalline form.

According to an embodiment, the present invention thus also concerns the crystalline form of the tetrahydrate of compound (A).

The crystalline form of the tetrahydrate of compound (A) is generally in the form of a powder, the features of which are improved in comparison with the free base form or other salts of compound (A). The tetrahydrate of compound (A) is stable for relative humidity ranging from at least 30% to 70% which is an improved property as compared to the hygroscopic nature of the previously described dihydrochloride. The tetrahydrate of compound (A) is also stable for temperatures ranging from 20° C. to 40° C.

The tetrahydrate of compound (A) exhibits one or more of the following features:

According to an embodiment, the tetrahydrate form of compound (A) exhibits a melting peak around 191° C. when measured by capillary tube method.

According to another embodiment, analysis by differential scanning calorimetry shows two endothermic events with onset around 53° C. and 83° C. which correspond to the loss of four water molecules; a last event is observed with an onset around 191° C.

According to another embodiment, the water content of the tetrahydrate of compound (A) is comprised between 14 and 16%, generally about 15.3±0.7% in weight.

According to another embodiment, the tetrahydrate form of compound (A) exhibits one or more of the powder X-ray diffractogram lines described below:

| Angle (2-Theta °) | d value (Angstrom) | Intensity (Count) | Relative Intensity (%) |
|---|---|---|---|
| 5.1 | 17.5 | 476 | 20.9 |
| 9.7 | 9.1 | 998 | 43.8 |
| 10.2 | 8.7 | 438 | 19.2 |
| 11.1 | 8.0 | 312 | 13.7 |
| 12.5 | 7.1 | 2276 | 100 |
| 13.1 | 6.8 | 517 | 22.7 |
| 14.6 | 6.1 | 700 | 30.8 |
| 15.2 | 5.8 | 624 | 27.4 |
| 15.8 | 5.6 | 375 | 16.5 |
| 16.5 | 5.4 | 1051 | 46.2 |
| 17.4 | 5.1 | 275 | 12.1 |
| 18.2 | 4.9 | 553 | 24.3 |
| 19.0 | 4.7 | 698 | 30.7 |
| 19.5 | 4.6 | 969 | 42.6 |
| 20.5 | 4.3 | 555 | 24.4 |

-continued

| Angle (2-Theta °) | d value (Angstrom) | Intensity (Count) | Relative Intensity (%) |
|---|---|---|---|
| 21.0 | 4.2 | 374 | 16.4 |
| 22.0 | 4.1 | 1000 | 43.9 |
| 22.5 | 3.9 | 446 | 19.6 |
| 23.7 | 3.8 | 467 | 20.5 |
| 24.3 | 3.7 | 588 | 25.8 |
| 24.8 | 3.6 | 1386 | 60.9 |
| 25.2 | 3.5 | 408 | 17.9 |
| 26.2 | 3.4 | 1352 | 59.4 |
| 26.7 | 3.3 | 370 | 16.3 |
| 27.2 | 3.3 | 292 | 12.8 |
| 27.5 | 3.2 | 336 | 14.8 |
| 28.4 | 3.1 | 1058 | 46.5 |
| 29.5 | 3.0 | 527 | 23.2 |

More particularly, the following peaks:

| 2-theta (°) | d (Ångstroms) |
|---|---|
| 9.7 | 9.1 |
| 12.5 | 7.1 |
| 14.6 | 6.1 |
| 15.2 | 5.8 |
| 16.5 | 5.4 |
| 19.0 | 4.7 |
| 19.5 | 4.6 |
| 22.0 | 4.1 |
| 24.3 | 3.7 |
| 24.8 | 3.6 |
| 26.2 | 3.4 |
| 28.4 | 3.1 |

According to a further object, the present invention also concerns processes of preparation of the tetrahydrate form of compound (A). The tetrahydrate of compound (A) can be prepared by usual methods such as insolubilisation from a solvent by concentration, addition of an anti-solvent, or lowering the temperature.

According to an embodiment, the process of preparation of the tetrahydrate form of compound (A) comprises the following steps:
dissolving compound (A) into water;
concentrating until the solid separates; and
drying the solid up to the desired final water content, such as 14-16%, particularly about 15.3±0.7% in weight.
Concentration may be generally achieved by evaporation.
According to another embodiment, the process comprising the following steps:
adding aqueous hydrochloric acid to the base form of compound (A);
adding acetone and seeding until the solid separates;
filtering; and
drying the solid up to the desired final water content, such as 14-16%, particularly about 15.3±0.7% in weight.
Compound (A) may be prepared as disclosed in WO 2006/117609.

The present invention also concerns the tetrahydrate of compound (A) for use for treating and/or preventing in a human patient disorders chosen from Alzheimer's disease; attention; wakefulness and memorization disorders; cognitive deficits in psychiatric pathologies; cognitive, mood and vigilance disorders in particular in aged persons; depressive or asthenic states; Parkinson's disease; obstructive sleep apnea; dementia with Lewy bodies; vascular dementia; vertigo; motion sickness; obesity; diabetes and the metabolic syndrome; sleep disorders; stress; psychotropic disorders; epilepsy; depression; narcolepsy with or without cataplexy; cognitive disorders in autism; substance abuse, notably alcohol abuse disorders; prevention of substance abuse withdrawal syndromes; post-stroke fatigue; attention and vigilance disorders of attention-deficit hyperactivity disorder (ADHD) in children or adults; disorders of the hypothalamohypophyseal secretion, the cerebral circulation and/or immune system; excessive daytime sleepiness, such as excessive daytime sleepiness and fatigue associated with Parkinson's disease, obstructive sleep apnea or dementia; and/or for facilitating night works or adaptation to time shift in healthy humans, where said use comprises the administration of the tetrahydrate of (A) in a human at a dose comprised between 10 and 90 µg a day (relative to the base of compound (A)).

According to an embodiment, the use is for treating and/or preventing sleep disorders such as insomnia, disorders of sleep initiation and maintenance, sleep fragmentation, parasomnias, sleep disordered breathing, circadian dysrhythmia, narcolepsy with or without cataplexy, excessive daytime sleepiness (including "sleep attacks"), such as excessive daytime sleepiness associated with Parkinson's disease, obstructive sleep apnea or dementia. Another use is for the treatment and/or prevention of substance abuse disorders, notably alcohol abuse. Another use is for the treatment and/or prevention of mood, cognitive and vigilance disorders associated with stroke. Another use is for treating and/or preventing cognitive and attention disorders in ADHD.

It is also disclosed herein a method of prevention and/or treatment of the above disorders comprising the administration of the tetrahydrate of compound (A) at a dose of the base comprised between 10 and 90 µg a day (relative to the base of compound (A)), with a pharmaceutically acceptable carrier or excipient, to a patient in the need thereof.

According to an embodiment, the daily dose of tetrahydrate of (A) for administration to a human is comprised between 20 and 50 µg a day, preferably 30 to 45 µg (relative to the base of compound (A)) a day.

According to another embodiment, the method of the invention may comprise the administration of the tetrahydrate of compound (A), at a frequency comprised between once every three days: once every other day (qod), once-a-day (qd). Preferably, the administration may thus take place once a day.

It is to be understood that the dose of the invention is the cumulative dose of each administration dose given within a day.

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

Actual dosage levels of the tetrahydrate of compound of formula (A) of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors, e.g. the condition of the patient.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of tetrahydrate of compound (A) which is required to achieve the desired biological effect will vary depending upon a number of factors, including the dosage of the drug to be administered, the type of disease, the disease state of the patient and the route of administration.

In general terms, the preferred dosage of a drug to be administered is likely to depend on such variables as the type and extent of progression of the disease or disorder, the overall health status of the particular patient, the relative biological efficacy of the compound selected, and formulation of the compound excipient, and its route of administration. The daily dose of the tetrahydrate of compound (A) will generally be lower than 90 µg a day per patient.

According to a further embodiment, the method of the invention also comprises the administration of one or more further active ingredient, selected from anti-Parkinson drugs such as levodopa, ropinorole, lisuride, bromocriptine, pramixepole or selected from anti-narcoleptic or purported anti-narcoleptic drugs from another class, including modafinil.

The tetrahydrate of compound (A) can be formulated into pharmaceutical compositions by admixture with one or more pharmaceutically acceptable excipients.

The compositions may conveniently be administered in unit dosage form and may be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

The tetrahydrate of compound (A) may be administered by various administration routes such as oral; parenteral including sub-cutaneous, intramuscular, intra-venous; sub-lingual, topical; local; intratracheal; intranasal; transdermal or rectal, the active ingredient being combined with a pharmaceutically acceptable excipient or vehicle in a pharmaceutical composition.

According to another object, the present invention thus also concerns the pharmaceutical composition comprising the tetrahydrate of the compound (A) and a pharmaceutically acceptable excipient or vehicle.

According to an embodiment, said composition is for use in treating and/or preventing the above disorders.

According to an embodiment, said composition is suitable for administration of the tetrahydrate of compound (A) at a dose comprised between 10 and 90 µg (relative to the base of compound (A)) a day.

For the topical application, the compositions of the invention may be formulated as creams, gels, ointments or lotions.

In particular, the formulations suitable for parenteral administration are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

According to the invention, oral administration of the compound or composition in an appropriate formulation is advantageously used. Formulations which are suitable to be administered orally to a patient include discrete units such as capsules, such as soft or hard gelatine capsules, tablets, each containing a predetermined amount of the tetrahydrate of compound of formula (A). They also include powders or granules; solutions or suspensions in an aqueous liquid or a non-aqueous liquid; or as an oil-in-water liquid emulsion or a water-in-oil liquid emulsion.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient, vehicle or carrier" includes in particular diluents, adjuvants, excipients, or vehicles. The use of such ingredients for pharmaceutical active substances is well known in the art.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with the above disorders. Preferably, the patient is a human.

Tetrahydrate of compound (A) may administered in unit dosage forms, wherein the term "unit dose" means a single dose which is capable of being administered to a patient, and which can be readily handled and packaged, remaining as a physically and chemically stable unit dose comprising either the active compound itself, or as a pharmaceutically acceptable composition.

The appropriate unitary dosage forms comprise the oral forms, the sublingual, buccal, intratracheal, intraocular, intranasal forms, the forms by inhalation, the topical, transdermal, sub-cutaneous forms, the parenteral forms, the rectal forms and the implants.

The daily dose of between 10 and 90 µg (relative to the base of compound (A)) according to the invention may be achieved by administering half a unit dosage form, a single unit dosage form or two or more unit dosage forms, according to the marketed unit dosage form, the daily dose to be administered and the frequency of administration that is prescribed by the practitioner.

FIGURES

The following examples are given for illustrative, non-limiting embodiments of the present invention.

DETAILED DESCRIPTION

Examples

Example 1

Synthesis of (3S)-4-{4-[3-(3-methylpiperidin-1-yl)propoxy]phenyl}pyridine 1-oxide, dihydrochloride, tetrahydrate 210±15 g of compound (A) and 200±10 g of water are charged in evaporation vessel. Temperature of bath in evaporation system is set to about 40° C. and mixture is agitated until all the precipitate is dissolved. Water is evaporated until product separates as solid form.

Evaporation vessel containing the product is transferred in vacuum tray drier and product is dried at 30° C. Product is transferred from evaporation vessel into actual drying vessel and drying is continued at 30° C. until water content of product is 15.3±0.7% in weight. Finally product is grinded and packed.

Example 2

Synthesis of (3S)-4-{4-[3-(3-methylpiperidin-1-yl)propoxy]phenyl}pyridine 1-oxide, dihydrochloride, tetrahydrate 2.5 kg of (3S)-4-{4-[3-(3-methylpiperidin-1-yl)propoxy]phenyl}pyridine 1-oxide are dissolved in hydrochloric acid solution and temperature is adjusted to 22-30° C. Acetone is added in the reactor, mixture is seeded and agitated. More acetone is added at 22-30° C. until total added amount is 20.0 kg. Temperature of mixture is adjusted to 18-24° C. and mixture is agitated for 1.0-2.0 h. Product is isolated by filtration and washed with a mixture of water and acetone. Product is dried under constant nitrogen flow at 20-30° C., grinded, and packed.

Example 3

X-Ray Powder Diffraction

X-Ray Powder Diffraction was recorded on (3S)-4-{4-[3-(3-methylpiperidin-1-yl)propoxy]phenyl}pyridine 1-oxide, dihydrochloride, tetrahydrate (Example 1) in the powder form.

Diffractometers Bruker D5000 Matic Diffractometer;
Cupper anode, 40 KV voltage, 40 mA intensity
θ-θ configuration, fixed sample
Ambient temperature
Range of measurement: 3° to 30° (2 theta)
Step incrementation: 0.04°
Measuring time by step: 4 s
No internal reference
Experimental treatment of the data by the EVA software (v 11.0)

Figure 1:
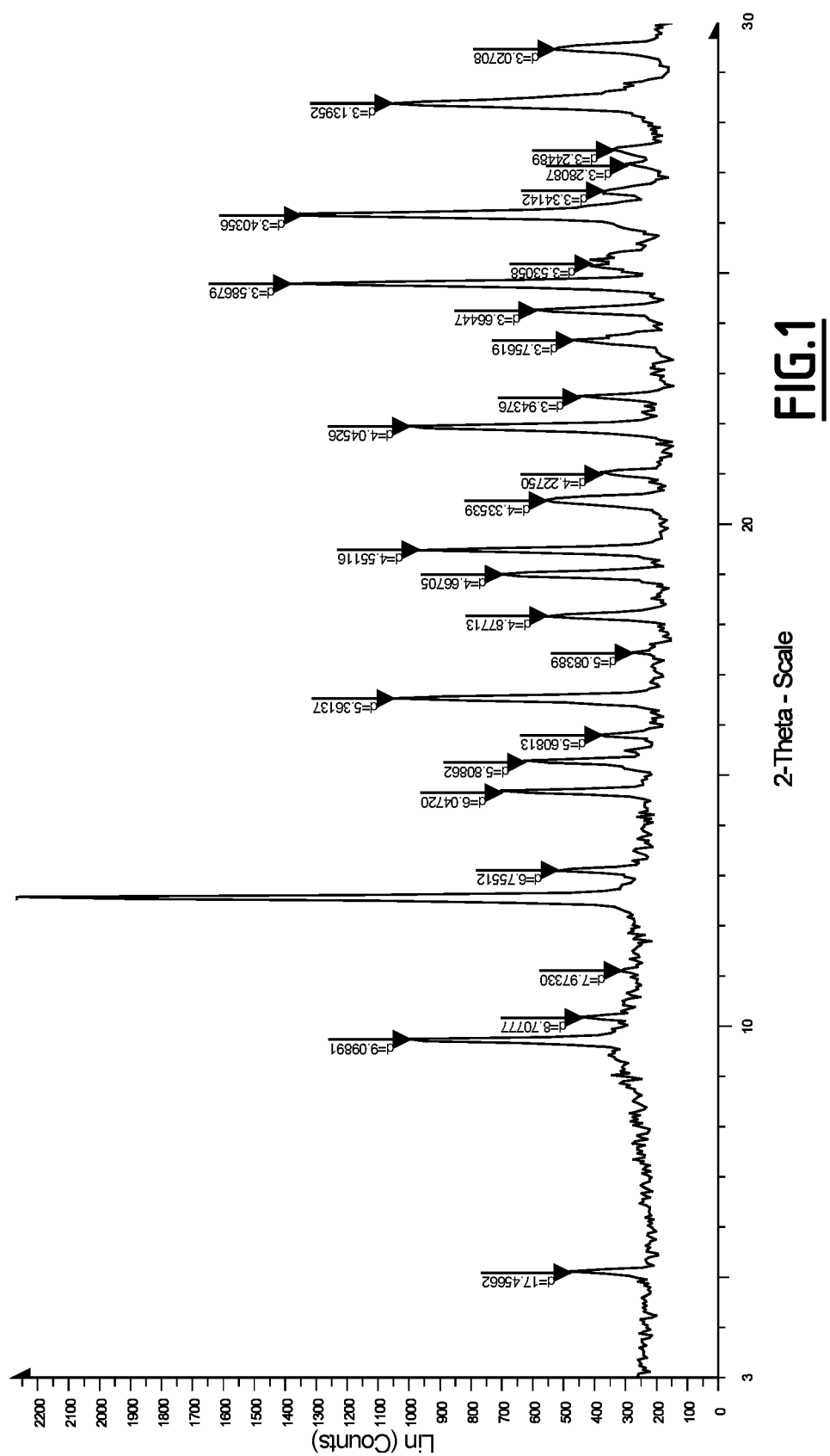
FIG. 1 illustrates the X-ray diffractogram (powder) of the compound obtained in Example 1 (tetrahydrate of compound (A)).
Figure 2:
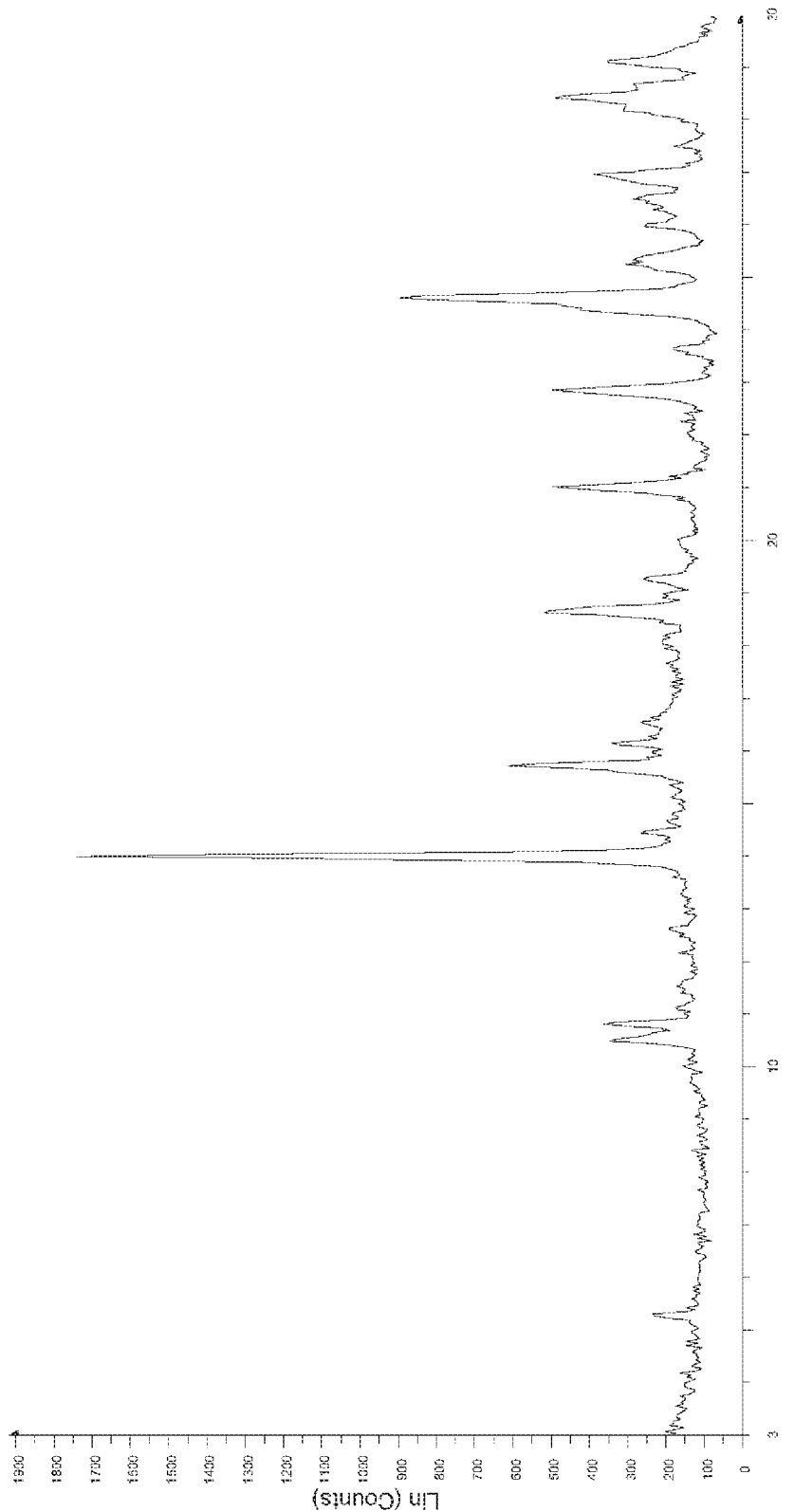
FIG. 2 illustrates the X-ray diffractogram (powder) of compound (A).

A typical diffractogram of (3S)-4-{4-[3-(3-methylpiperidin-1-yl)propoxy]phenyl}pyridine 1-oxide, dihydrochloride, tetrahydrate is depicted in FIG. 1 which is clearly different from the non tetrahydrate form of (3S)-4-{4-[3-(3-methylpiperidin-1-yl)propoxy]phenyl}pyridine 1-oxide, dihydrochloride displayed in FIG. 2.

Characterizing peaks of (3S)-4-{4-[3-(3-methylpiperidin-1-yl)propoxy]phenyl}pyridine 1-oxide, dihydrochloride, tetrahydrate include:

| Angle (2-Theta °) | d value (Angstrom) | Intensity (Count) | Relative Intensity (%) |
|---|---|---|---|
| 5.1 | 17.5 | 476 | 20.9 |
| 9.7 | 9.1 | 998 | 43.8 |
| 10.2 | 8.7 | 438 | 19.2 |
| 11.1 | 8.0 | 312 | 13.7 |
| 12.5 | 7.1 | 2276 | 100 |
| 13.1 | 6.8 | 517 | 22.7 |
| 14.6 | 6.1 | 700 | 30.8 |
| 15.2 | 5.8 | 624 | 27.4 |
| 15.8 | 5.6 | 375 | 16.5 |
| 16.5 | 5.4 | 1051 | 46.2 |
| 17.4 | 5.1 | 275 | 12.1 |
| 18.2 | 4.9 | 553 | 24.3 |
| 19.0 | 4.7 | 698 | 30.7 |
| 19.5 | 4.6 | 969 | 42.6 |
| 20.5 | 4.3 | 555 | 24.4 |
| 21.0 | 4.2 | 374 | 16.4 |
| 22.0 | 4.1 | 1000 | 43.9 |
| 22.5 | 3.9 | 446 | 19.6 |
| 23.7 | 3.8 | 467 | 20.5 |
| 24.3 | 3.7 | 588 | 25.8 |
| 24.8 | 3.6 | 1386 | 60.9 |
| 25.2 | 3.5 | 408 | 17.9 |
| 26.2 | 3.4 | 1352 | 59.4 |
| 26.7 | 3.3 | 370 | 16.3 |
| 27.2 | 3.3 | 292 | 12.8 |
| 27.5 | 3.2 | 336 | 14.8 |
| 28.4 | 3.1 | 1058 | 46.5 |
| 29.5 | 3.0 | 527 | 23.2 |

Example 4

Characterization of (3S)-4-{4-[3-(3-methylpiperidin-1-yl)propoxy]phenyl}pyridine 1-oxide, dihydrochloride, tetrahydrate Microanalysis The dihydrochloride salt disclosed in example 52 of WO 2006/117609 has been analyzed by microanalysis. Results can be compared with theoretical values for anhydrous and tetrahydrate dihydrochloride:

| | Ponderal (%) composition | | |
|---|---|---|---|
| element | found | theory for anhydrous dihydrochloride | theory for dihydrochloride tetrahydrate |
| C | 58.3 | 60.1 | 51.0 |
| H | 7.0 | 7.1 | 7.7 |
| Cl | 17.8 | 17.7 | 15.0 |

The measured values fit well with the theoretical ones for the anhydrous dihydrochloride and are clearly different from those of the dihydrochloride tetrahydrate.

The compound disclosed in example 52 of WO 2006/117609 is therefore not in a tetrahydrate form.

Chloride Titration

Chloride titration with silver nitrate was carried out for present Example 1 and previous Example 52 of WO 2006/117609.

The content of chloride for present Example 1 was 15.0% just as the theoretical value.

The content of chloride for Example 52 of WO 2006/117609 was 17.8% for a theoretical value of 17.75%.

Example 1 is different from the compounds previously described in Example 50 (the free base and the oxalate salt which do not contain chloride) and Example 52 of WO 2006/117609.

Melting Points

|  | Melting points |
| --- | --- |
| Example 51 of WO 2006/117609 | 74° C. |
| Example 52 of WO 2006/117609 | 193° C. |
| Present Example 1 | 193° C. |

The comparison of melting points evidences that present Example 1 is distinct from Example 51 of WO 2006/117609.

Water Titration (by Karl Fischer)

|  | Water content (% in weight) - Measured | Water content (% in weight) - Theory |
| --- | --- | --- |
| Present Example 1 | 16.0% (i.e. 15.3 +/− 0.7%) | 15.3% |
| Example 52 of WO 2006/117609 | 4 | 0% |

Water titration clearly shows that the new phase is a tetrahydrate whereas the Example 52 of WO 2006/117609 was not.

Example 5

Stability

Stability of Example 52 of WO 2006/117609
Stability studies have been performed according to ICH. At 40° C./75% relative humidity, some degradation is observed:

| time (months) | purity on anhydrous substance |
| --- | --- |
| 0 | 100.2 |
| 1 | 100.8 |
| 3 | 98.2 |
| 6 | 98.4 |

Similar results were obtained for the 3 months sample at 30° C./65% relative humidity:

| time (months) | purity on anhydrous substance |
| --- | --- |
| 0 | 100.2 |
| 3 | 98.4 |

The stability studies thus show a trend to decomposition of Example 52. The substance remains within the specifications 98.0-102.0%, but the decrease in purity is significant and could lead to a reduced shelf life.

Stability of Present Example 1
Stability has been assessed under ICH conditions.
Results at 40° C./75% relative humidity are displayed in the table below: no degradation is observed:

| time (months) | purity on anhydrous substance |
| --- | --- |
| 0 | 99.6 |
| 1 | 100.3 |
| 3 | 99.7 |
| 6 | 100.3 |

There is no significant variation of the purity over the time. The dihydrochloride tetrahydrate is more stable than the previously described phase (Example 52 of WO 2006/117609) which lost 2% within six months.

Furthermore, analysis of present Example 1 by dynamic vapor sorption and X-ray powder diffraction showed that the tetrahydrate form displays a good stability for relative humidity from 10 to 90% at 25° C.

Example 6

Hygroscopy

Example 52 of WO 2006/117609

This compound is hygroscopic. It uptakes water during time.

A batch that was prepared and stored under Good Manufacturing Practice and was found to display increasing amounts of water content over time:

| time (months) | water content (% in weight) |
| --- | --- |
| 0 | 1 |
| 6 | 2 |
| 11 | 4 |

This could not be cured by drying at it was found that it leads to some degradation as shown in the tables below.

Drying was not complete at 60° C. over 24 hours. Drying at 80° C. or 100° C. allowed the complete removal of water, but some decomposition occurred.

Drying at 60° C.

| time (hr) | Main impurity (%) |
| --- | --- |
| 0 | 0.08 |
| 8 | 0.08 |
| 12 | 0.08 |
| 24 | 0.10 |

Drying at 80° C.

| time (hr) | Main impurity (%) |
| --- | --- |
| 0 | 0.08 |
| 8 | 0.11 |
| 16 | 0.12 |
| 24 | 0.14 |

Drying at 100° C.

| time (hr) | Main impurity (%) |
| --- | --- |
| 0 | 0.08 |
| 8 | 0.32 |
| 16 | 0.44 |

Present Example 1

Example 1 is not hygroscopic.
At 40° C./75% relative humidity, no water content modification is observed:

| time (months) | water content (% in weight) |
|---|---|
| 0 | 16 |
| 1 | 16 |
| 3 | 15 |
| 6 | 16 |
| 12 | 15 |

The tetrahydrate form of (3S)-4-{4-[3-(3-methylpiperidin-1-yl)propoxy]phenyl}pyridine 1-oxide, dihydrochloride is thus more stable than (3S)-4-{4-[3-(3-methylpiperidin-1-yl)propoxy]phenyl}pyridine 1-oxide, dihydrochloride.

The tetrahydrate displays enhanced properties for pharmaceutical development and displays enhanced properties for pharmaceutical development.

The invention claimed is:

1. The tetrahydrate form of the compound of formula (A):

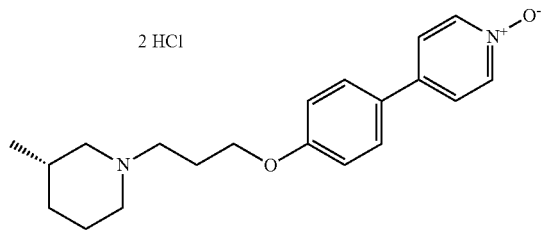 [SMILES: C[C@H]1CCCN(CCCOc2ccc(-c3cc[n+]([O-])cc3)cc2)C1]

(A): (3S)-4-{4-[3-(3-methylpiperidin-1-yl)propoxy]phenyl}pyridine 1-oxide, dihydrochloride.

2. The tetrahydrate form according to claim 1 which exhibits a melting peak of 191° C. when measured by capillary tube method.

3. The tetrahydrate form according to claim 1 which comprises a water content of 15.3±0.7% in weight.

4. The tetrahydrate form according to claim 1 which exhibits the powder X-ray diffractogram lines: 2-Theta° (d in Ångstroms)=9.7 (9.1), 12.5 (7.1), 14.6 (6.1), 15.2 (5.8), 16.5 (5.4), 19.0 (4.7), 19.5 (4.6), 22.0 (4.1), 24.3 (3.7), 24.8 (3.6), 26.2 (3.4), 28.4 (3.1).

5. A process of preparation of the tetrahydrate form according to claim 1 comprising the following steps:
dissolving compound (A) in water;
concentrating up to crystallization;
filtering; and
drying.

6. A process of preparation of the tetrahydrate form according to claim 1 comprising the following steps:
dissolving compound (A) in water;
adding acetone and lowering temperature up to crystallization;
filtering; and
drying.

7. A pharmaceutical composition comprising the tetrahydrate form according to claim 1, together with at least one pharmaceutically acceptable excipient.

8. A method for treating Alzheimer's disease; attention; wakefulness and memorization disorders; cognitive deficits in psychiatric pathologies; mood, vigilance or cognitive disorders in aged persons; depressive or asthenic states; Parkinson's disease; obstructive sleep apnea; dementia with Lewy bodies; vascular dementia; vertigo; motion sickness; obesity; diabetes and the metabolic syndrome; sleep disorders; stress; psychotropic disorders; epilepsy; depression; narcolepsy with or without cataplexy; disorders of the hypothalamohypophyseal secretion, the cerebral circulation and/or immune system; excessive daytime sleepiness and fatigue associated with Parkinson's disease, obstructive sleep apnea or dementia and/or for facilitating night works or adaptation to time shift in healthy humans; attention deficit disorders; substance abuse abuse disorders; substance abuse withdrawal syndromes; post-stroke fatigue, mood, cognitive and vigilance disorders; cognitive disorders in autism; attention and vigilance disorders of attention-deficit hyperactivity disorder (ADHD) in children or adults, said method comprising:
administering the tetrahydrate form according to claim 1 to a human patient in need thereof.

9. A method for treating sleep disorders, insomnia, disorders of sleep initiation and maintenance, sleep fragmentation, parasomnias, sleep disordered breathing, circadian dysrhythmia, narcolepsy with or without cataplexy, excessive daytime sleepiness, excessive daytime sleepiness associated with Parkinson's disease, obstructive sleep apnea or dementia; substance abuse disorders, alcohol abuse, mood cognitive and vigilance disorders associated with stroke; cognitive and attention disorders in ADHD,
said method comprising administering the tetrahydrate form according to claim 1 to a human patient in need thereof.

10. The method according to claim 8 comprising the administration of said tetrahydrate of compound (A) in a human at a dose comprised between 10 and 90 μg relative to the base of compound (A) a day.

11. The tetrahydrate form of the compound of formula (A):

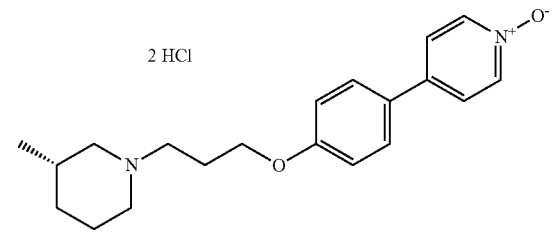 [SMILES: C[C@H]1CCCN(CCCOc2ccc(-c3cc[n+]([O-])cc3)cc2)C1]

(A): (3S)-4-{4-[3-(3-methylpiperidin-1-yl)propoxy]phenyl}pyridine 1-oxide, dihydrochloride, which exhibits the powder X-ray diffractogram lines: 2-Theta° (d in Ångstroms)=9.7 (9.1), 12.5 (7.1), 14.6 (6.1), 15.2 (5.8), 16.5 (5.4), 19.0 (4.7), 19.5 (4.6), 22.0 (4.1), 24.3 (3.7), 24.8 (3.6), 26.2 (3.4), 28.4 (3.1).

* * * * *